United States Patent [19]
Humphrey et al.

[11] Patent Number: 5,908,936
[45] Date of Patent: Jun. 1, 1999

[54] PROCESS FOR SYNTHESIZING CARBAPENEM INTERMEDIATES

[75] Inventors: Guy R. Humphrey, Belle Mead; Ross A. Miller, Fanwood, both of N.J.; David R. Lieberman, Barnet, United Kingdom

[73] Assignee: Merck & Co., Inc., Rahway, N.J.

[21] Appl. No.: 09/076,949

[22] Filed: May 13, 1998

Related U.S. Application Data

[60] Provisional application No. 60/046,357, May 13, 1997.
[51] Int. Cl.$^6$ .................................................. C07D 275/06
[52] U.S. Cl. ............................................................ 548/208
[58] Field of Search ............................................... 548/208

[56] References Cited

U.S. PATENT DOCUMENTS 2,773,765  12/1956  Oskar et al. ................................. 96/33

FOREIGN PATENT DOCUMENTS

WO 97/40048  10/1997  WIPO .

OTHER PUBLICATIONS

Paul Cagniant, et al., *Bull. de la Soc., Chim. de France*, pp. 2037–2042 (1966).
R. E. Steiner, *Hel. Chim AACTA* 17 pp. 1142–1157, (1934), *Chem. Abst.*, 29(4) (1935).
S. M Schmitt et al., *J. Antibiotics*, 41(6), pp. 780–787 (1998).

*Primary Examiner*—Laura L. Stockton
*Attorney, Agent, or Firm*—Sylvia A. Ayler; Mark R. Daniel

[57] ABSTRACT

A process for synthesizing a compound of formula I:

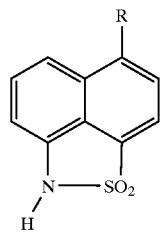

is disclosed wherein R represents halo or $C_{1-6}$ alkyl, unsubstituted or substituted with OP, wherein P represents a protecting group.

19 Claims, No Drawings

PROCESS FOR SYNTHESIZING CARBAPENEM INTERMEDIATES

This application claims the benefit of U.S. Provisional Application Ser. No. 60/046,357, filed May 13, 1997.

BACKGROUND OF THE INVENTION

The invention described herein relates to intermediate compounds that are useful in the synthesis of carbapenems. Carbapenems are antibiotics having a broad antibacterial spectrum, which includes gram positive, gram negative and anaerobic microorganisms.

The carbapenems in which the naphthosultams of the present invention are useful contain a naphthosultam ring system in the side chain which is attached to the carbapenem nucleus at position two. Examples of carbapenems which are substituted with a naphthosultam-containing side chain at position two are found in U.S. application Ser. No. 60/016,184 filed on Apr. 24, 1996, the teachings of which are hereby incorporated by reference. The naphthosultam platform is attached to the carbapenem nucleus directly or through a linking moiety, such as a sulfur atom, a methylene group or a higher alkylene group.

Also attached to the naphthosultam platform may be one or more substituent groups. The naphthosultam produced is an active pharmacophore when appropriately coupled to a carbapenem.

SUMMARY OF THE INVENTION

A process for synthesizing a compound of formula I:

[Structure I: naphthosultam with R substituent, N—SO₂, NH]

is disclosed wherein R represents halo or $C_{1-6}$ alkyl, unsubstituted or substituted with OP, wherein P represents a protecting group, comprising:

(a) reacting a compound of the formula II:

[Structure II: naphthalene with R substituent]

wherein R is as previously defined, with chlorosulfonic acid to produce a compound of formula III:

[Structure III: naphthalene with R and SO₂Cl substituents]

(b) reacting compound III with $NHR^aR^b$, wherein $R^a$ and $R^b$ represent H or $C_{1-6}$ alkyl, to produce a compound of formula IV;

[Structure IV: naphthalene with R and $SO_2NR^aR^b$ substituents]

(c) reacting compound IV with $HNO_3$ to produce a compound of formula V:

[Structure V: naphthalene with R, $NO_2$, and $SO_2NR^aR^b$ substituents]

(d) reacting compound V with a reducing agent to produce a compound of formula VI:

[Structure VI: naphthalene with R, $NH_2$, and $SO_2NR^aR^b$ substituents]

and (e) reacting compound VI with acid to produce a compound of formula I.

Intermediate compounds that are useful in the synthesis of carbapenem side chains are included as well.

DETAILED DESCRIPTION OF THE INVENTION

The invention is described using the following definitions unless otherwise indicated.

Alkyl refers to $C_{1-6}$ alkyl groups which may be straight or branched.

Halogen and halo refer to chlorine, bromine and iodine, selected on an independent basis. Preferred values of halo include bromo and iodo. Most preferably, halo is bromo.

Acid as used herein refers to strong acids such as hydrochloric, formic, sulfuric, toluene sulfonic acid and the like.

The process described herein involves the cyclization of an appropriately substituted naphthalene sulfonamide to provide appropriately substituted 1,8-naphthosultams. In one aspect of the invention, the invention involves synthesizing a compound of formula I:

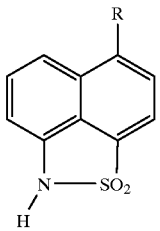

wherein R represents halo or $C_{1-6}$ alkyl, unsubstituted or substituted with OP, wherein P represents a protecting group, comprising:

(a) reacting a compound of the formula II:

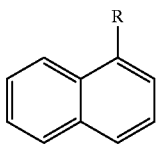

wherein R is as previously defined, with chlorosulfonic acid to produce a compound of formula III:

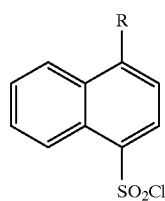

(b) reacting compound III with $NHR^aR^b$, wherein $R^a$ and $R^b$ represent H or $C_{1-6}$ alkyl, to produce a compound of formula IV;

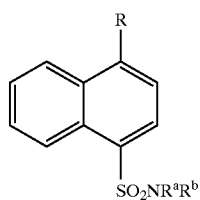

(c) reacting compound IV with $HNO_3$ to produce a compound of formula V:

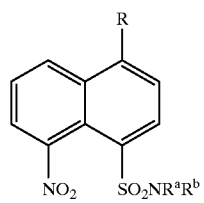

(d) reacting compound V with a reducing agent to produce a compound of formula VI:

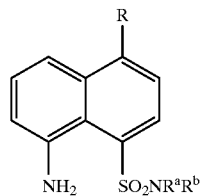

and (e) reacting compound VI with acid to produce a compound of formula I.

In a preferred aspect of the invention, R represents methyl. In another preferred aspect of the invention, R represents halo, preferably Br or I, and most preferably Br.

In another preferred aspect of the invention, one of $R^a$ and $R^b$ represent H or $C_{1-6}$ alkyl, and the other is $C_{1-6}$ alkyl. More particularly, both represent $C_{1-6}$ alkyl, and most preferably, both represent ethyl.

In another preferred aspect of the invention, a process of making a compound of formula X:

is included herein which comprises reacting a compound of the formula XI:

with a lithiating agent to produce a compound of the formula XII:

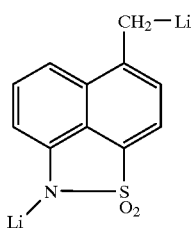

reacting the lithiated compound with CO₂ to produce a compound of the formula:

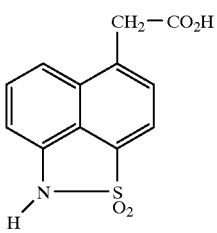

and reducing this compound with a reducing agent to produce a compound of formula X.

In another preferred aspect of the invention, a process of making a compound of formula X:

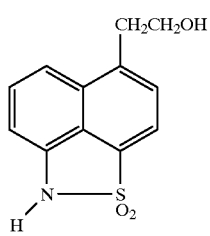

is included herein which comprises reacting a compound of the formula XI:

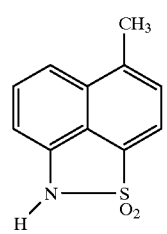

with a lithiating agent to produce a compound of the formula XII:

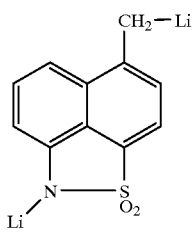

reacting the lithiated compound with HCHO to produce a compound of the formula:

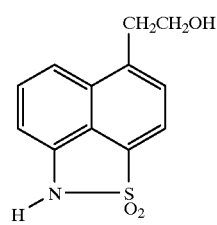

In another aspect of the invention, an intermediate compound is included which is represented by the formula I:

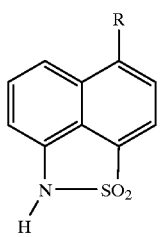

wherein R represents halo or $C_{1-6}$ alkyl, unsubstituted or substituted with OP, wherein P represents a protecting group.

In another aspect of the invention, an intermediate compound is included which is represented by formula V:

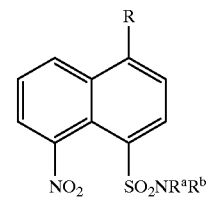

wherein

R represents halo or $C_{1-6}$ alkyl, unsubstituted or substituted with OP, wherein P represents a protecting group;

and $R^a$ and $R^b$ represent H or $C_{1-6}$ alkyl.

In another aspect of the invention, an intermediate compound is included which is represented by formula XI:

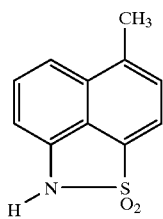

XI

In another aspect of the invention, an intermediate compound is included which is represented by formula XII:

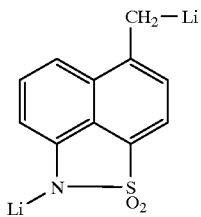

XII

In another aspect of the invention, intermediate compounds are included which are represented by the formulae:

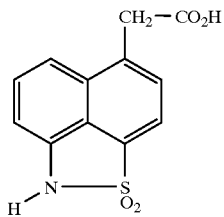

XIV

Generally the reaction between the 1-halonaphthalene or 1-alkylnaphthalene and the chlorosulfonic acid can be conducted in an organic solvent, such as nitro substituted organics, e.g., nitromethane and nitrobenzene, and halo substituted organic solvents, such as dichlorobenzene, including ortho, meta or para substituted benzene, dichloromethane, chloroform, carbon tetrachloride, dichloroethane and trifluoroacetic acid (TFA). Preferably TFA is used as the solvent.

The reaction is typically conducted at a temperature of from about −40° C. to as high as about 100° C., preferably about 0° C. to about 25° C.

The formation of the sulfonamide is typically conducted in a non-reactive organic solvent. Examples include secondary and tertiary alcohols, such as isopropanol, tertiary butanol, aromatics, such as toluene, and xylene, hexanes, ethers, esters, tetrahydrofuran, and many chlorinated solvents, as described above. The reaction is typically conducted between about −50° C. and reflux temperature.

The reaction with nitric acid is typically conducted in trifluoroacetic acid, sulfuric acid, nitrobenzene or a chlorinated organic solvent, as described above. The temperature range is typically from about −30° C. to about 60° C., and more preferably from about 0° C. to about 20° C.

Reduction of the nitro group to form an amine and cyclization can be conducted in essentially any solvent, at a temperature ranging from about −40° C. to reflux temperature.

Reducing agents which are useful in connection with the present invention include, for example, $H_2$/Pd as well as any other catalyst, Pd/C with chemical transfer reagents, such as formic acid, ammonium formate, any metal formate, any trialkylammonium formate or cyclohexene, tin chloride and the like.

Acids which are useful for the cyclization include for example, hydrochloric, sulfuric, trifluoroacetic and methanesulfonic acids. Preferably hydrochloric acid is used.

Carboxylation (chain extension) can typically be conducted in solvents such as THF and ether, e.g., diethylether, at a temperature generally in the range of about −100° C. to about 70° C. The base that is included in the reaction is typically lithium dialkylamide, e.g., lithium diisopropylamide.

Reduction of the carboxylic acid to form the alcohol is typically conducted in a solvent such as THF or diethylether. Suitable reducing agents include borane in THF and similar agents. This reaction is typically conducted at a temperature ranging from about −50° C. to reflux temperature.

The carbapenems which are synthesized in accordance with the present invention are prepared by reacting a suitably protected, activated 2-hydroxymethyl-carbapen-2-em-3-carboxylate with a naphthosultam, modifying the thus-introduced side chain as desired, and then removing any protecting groups which are present to afford the desired final product. The process is illustrated by the following generic scheme:

FLOW SHEET A

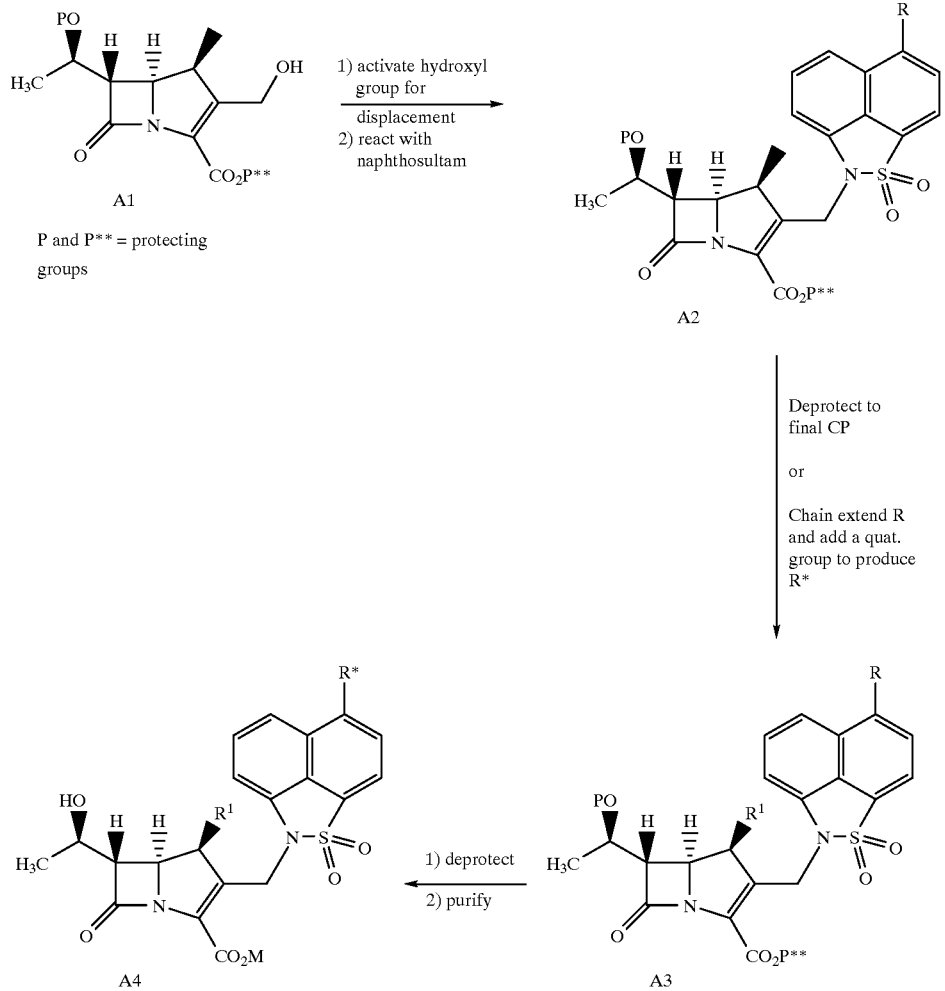

With reference to Flow Sheet A above, the naphthosultam side chain group can initially be reacted with a suitably protected carbapen-2-em-3-carboxylate having an activated hydroxymethyl group at the 2-position.

The carbapenem nucleus having a —CH$_2$H substituent at position 2 can be obtained in accordance with Schmitt, S. M. et al., *J. Antibiotics* 41(6): 780–787 (1988), the teachings of which are incorporated herein by reference. The carboxylic acid group at C-3 of the carbapenem is generally protected as a carboxyl protecting group such as p-nitrobenzyl (PNB), allyl, p-methoxybenzyl, trichloroethyl, 2-trimethylsilylethyl, and the like. Furthermore, the hydroxyl group of the 6-(hydroxyethyl) side-chain is optionally protected with a hydroxyl protecting group such as trimethylsilyl (TMS), triethylsilyl (TES), tert-butyldimethylsilyl (TBDMS), tert-butyldiphenylsilyl (TBDPS), acetyl, allyloxycarbonyl, 2-trimethylsilylethoxy carbonyl, 2-trichloroethoxycarbonyl and the like.

The addition of the naphthosultam side chain group (SCG) to the carbapenem is accomplished by treating a solution of the hydroxymethyl-carbapenem and the naphthosultam side chain group in a suitable solvent such as tetrahydrofuran (THF), ether, acetonitrile, dimethylformamide (DMF), benzene, dimethylsulfoxide (DMSO), and the like with a (premixed) suitable activating reagent such as diethyl azodicarboxylate (DEAD)/triphenylphosphine, diisopropyl azodicarboxylate (DIAD)/tributylphosphine, and the like, at a temperature between about −20° C. and 35° C. for about 5 to 90 minutes.

Alternatively, the naphthosultam and carbapenem can be mixed together with either the azodicarboxylate or the phosphine reagent in a suitable and the other component of the activating reagent (the phosphine or the azodicarboxylate, respectively) can be added to that mixture. Once the naphthosultam, carbapenem, and activating reagent(s) have been mixed, the reaction is allowed to proceed at a temperature between about −20° C. and 35° C. for about 5 to 90 minutes.

The resulting mixture is then subjected to a standard work-up procedure to afford a crude 2-naphthosultam-methyl substituted carbapenem which is purified, if necessary, by recrystallization or by chromatography on silica gel, eluting with a suitable solvent or mixture of two or more solvents, such as hexane, ethyl acetate, ether, benzene, dichloromethane, chloroform, acetone, methanol and the like.

Modification of the naphthosultam side chain of compounds, which is generally necessary to introduce the charged substituent, is best accomplished before removal of the protecting groups. For compounds which contain a hydroxyl group in the side chain, a positively charged substituent may be introduced into the side chain by first activating the hydroxyl group by converting it to a suitable leaving group such as a triflate, mesylate, tosylate, iodide, chloride, bromide, and the like, and then displacing the resulting leaving group with a quaternizing compound, such as N-methyl-imidazole, N-(2-hydroxyethyl)-imidazole, N-methyl-diazabicyclooctane, 1-(carbamoylmethyl)-4-aza-1-azoniabicyclo-[2.2.2.]-octane, 1-(3-hydroxyprop-1 -yl)-4-aza-1-azoniabicyclo-[2.2.2.]-octane, pyridine, morpholine and the like which contains a nitrogen atom that can act as a nucleophile.

Alternatively, the charged substituent may be incorporated in the naphthosultam side chain before addition of the naphthosultam to the carbapenem or may be introduced after deprotection. Introduction of the charged substituent before deprotection is greatly preferred.

The conversion of the hydroxyl group to a suitable leaving group is accomplished by treating the hydroxyl substituted compound in a suitable solvent such as dichloromethane, tetrahydro-furan, ether, benzene, and the like with an activating reagent, such as trifluoromethanesulfonic anhydride, methanesulfonic anhydride, toluenesulfonic anhydride, methanesulfonyl chloride, benzenesulfonyl chloride, toluenesulfonyl chloride, and the like in the presence of a suitable base such as triethylamine, tributylamine, diisopropylethyl-amine, and the like at a temperature between about −100° C. and 0° C. for about 5 to 120 minutes. The intermediate thus obtained contains a leaving group, which may be converted to an alternative leaving group, iodide, by treating a solution of the intermediate in a suitable solvent such as acetone, methyl ethyl ketone, and the like at about −10° C. to 50° C. with an excess of sodium iodide or potassium iodide for about 0.25 to 24 hours.

In many cases, the iodide is obtained in sufficiently pure form that it may be used without further purification. For ease of handling, the iodide, if not crystalline, may be lyophilized from benzene to afford an amorphous, easily handled, solid.

The activated hydroxyl group or iodide is displaced by reacting the activated intermediate with activating reagent. In some cases, activation and displacement may be accomplished in a single step. The activating reagent is added to a solution of the hydroxyl substituted compound in the presence of a suitable base in a suitable solvent such as dichloromethane, tetrahydrofuran, ether, DMF, benzene, acetonitrile, DMSO, and the like. The resulting activated intermediate is treated with 1–3 molar equivalents of the naphthosultam at a temperature between about −78° C. and 50° C. for about 15 to 120 minutes. In some cases, it is desirable to form the activated intermediate in one solvent, isolate the activated intermediate, and conduct the displacement reaction in a different solvent. In other cases, the displacement may be conducted without isolation of the intermediate and, in cases where Q* is also used as a base, may even be concurrent with the formation of the activated intermediate.

In cases where the displacement reaction is best accomplished by using the iodide, a solution of the iodide is combined with an approximately equivalent amount (0.9–1.05 molar equivalents) of the naphthosultam. A salt of a non-nucleophilic acid, such as silver trifluoromethanesulfonate, silver tetrafluoroborate and the like can be added. Although the reaction will proceed in the absence of the silver salt, the reaction proceeds more rapidly in the presence of an appropriate salt. In addition, the salt assists in the removal of the displaced iodide from the reaction mixture which can improve the efficiency of subsequent steps. The resulting mixture is then subjected to a standard work-up procedure familiar to those skilled in the art to afford a crude product which is purified, if necessary, by recrystallization or chromatography.

An alternative method for introducing a positive charge into the side chain may be applied to side chains that contain a nitrogen atom which may be quaternized by reaction with a suitable alkylating reagent, such as methyl iodide, methyl bromide, benzyl trichloroacetimidate, methyl trifluoromethanesulfonate, triethyloxonium tetrafluoroborate, and the like. Quaternization of the nitrogen atom in the side chain is effected by treating a solution of the compound with a slight excess (1.05 to 1.2 molar equivalents) of the alkylating reagent.

The synthesis of the target compound is typically completed by removing any protecting groups which are present in the penultimate intermediate using standard techniques which are well known to those skilled in the art. The deprotected final product is then purified, as necessary, using standard techniques such as ion exchange chromatography, HPLC on reverse phase silica gel, MPLC on reverse phase polystyrene gel, and the like or by recrystallization.

The final product may be characterized structurally by standard techniques such as NMR, IR, MS, and UV. For ease of handling, the final product, if not crystalline, may be lyophilized from water to afford an amorphous, easily handled solid.

Preferred values of R include halo, methyl, ethyl and propyl, unsubstituted or substituted with OP, wherein P represents a hydroxyl protecting group.

Representative examples of protecting groups P include trimethylsilyl (TMS), triethylsilyl (TES), tert-butyldimethylsilyl (TBDMS), tert-butyldiphenylsilyl (TBDPS), acetyl, allyloxycarbonyl, 2-trimethylsilylethoxy carbonyl, 2-trichloroethoxycarbonyl and the like.

Preferred values of $R^a$ and $R^b$ include H, methyl, ethyl and propyl. Most preferably each represents ethyl. Thus, preferably $NHR^aR^b$ represents dimethylamine, diethylamine or dipropylamine.

As used herein, the term "reducing agent" is used to refer to compounds which when reacted with compound V, convert the nitro group at position 8 to an amino group. Examples of suitable reducing agents include $H_2$ in combination with a metal, e.g., Pd/C, formic acid in combination with a metal, trialkylammonium formates with a metal, cyclohexene and a metal, tin chloride and the like.

EXAMPLE 1

CHLOROSULFONATION

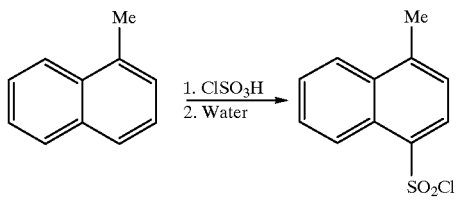

A three neck flask was charged with methylnaphthalene (2.63 Kg) and trifluoroacetic acid (13.2 L). The two-phase mixture was stirred and cooled to 5° C. using an ice-water bath. Chlorosulfonic acid (2.93 L) was added over 30 minutes maintaining the reaction temperature at <20° C. The reaction was quenched with deionized water at 10–20° C. over 15 min.

The product crystallized upon addition to water to give a white slurry.

The reaction vessel was washed with TFA/water (1:1, 1.0 L) and the wash added to the quench vessel. The cake was filtered on a polypropylene filter cloth and washed with water. The cake was dried in nitrogen stream overnight.

EXAMPLE 2

SULFONAMIDE

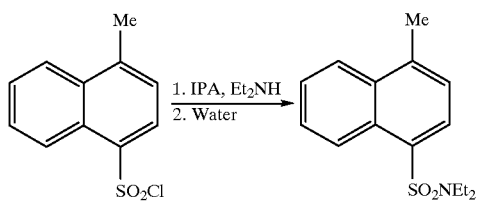

A flask was charged with methylnaphthalenesulfonyl chloride (4.0 Kg) and isopopanol (12.0 L). Diethylamine (3.73 L) was added to the slurry over 10 min.

An exotherm to about 65° C. occured and the starting material dissolved. The reaction progress was monitored by HPLC.

The solution was cooled to 20° C. and water (4 L) added. The mixture was seeded with sulfonamide product (2 gm) and aged at 20° C. for 20 min. The remaining water (32 L) was added over 1 h. The resultant slurry was aged at 20° C. for 20 min.

The slurry was filtered on a 23" polypropylene filter cloth and washed with water (12 L). The cake was dried in nitrogen stream overnight.

EXAMPLE 3

NITRATION

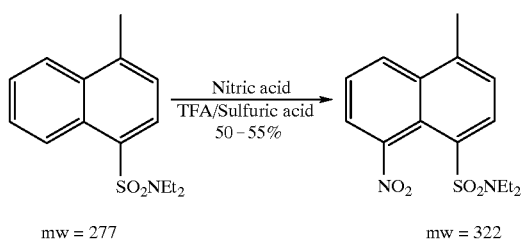

A 2 L flask, fitted with nitrogen inlet, mechanical stirrer, addition funnel and temperature probe was charged with N,N-Diethyl-1-Methyl-4-naphthalenesulfonamide (30 gms) and trifluoroacetic acid (TFA) (150 mL). The resultant solution was cooled to 15° C. Concentrated sulfuric acid (30 mL) was added over 2 minutes. The solution was cooled to −3° C.

Fuming nitric acid (6.2 mL) was added to the solution with rapid stirring over about 30 min maintaining the reaction temperature at −3 to +5° C.

The reaction progress was monitored by HPLC. The reaction was considered complete when <1% starting material remained by HPLC analysis (by area relative to product at 200 nm).

Water (375 mL) was added to the solution over 60 min. maintaining the quench temperature less than 25° C. using ice-water bath. The resultant slurry was aged at 20° C. for 30 min, filtered and the cake washed with water (100 mL).

The cake was dried in a nitrogen stream until the residual water content was <35% w/w.

The partially dried solid was slurried in ethyl acetate (75 mL) at 30° C. for 30 min. Hexane (150 mL) was added over 20 min and the slurry aged at 20° C. for 30 min. The slurry was filtered, washed with hexane (100 mL) and dried in a nitrogen stream overnight.

EXAMPLE 4

REDUCTION-CYCLIZATION

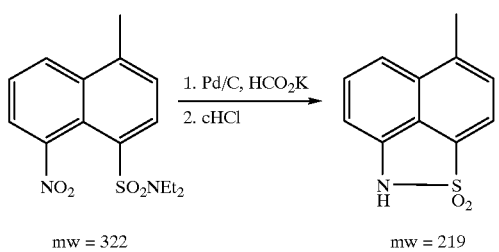

A 72 L round bottom flask was equipped with a $N_2$ inlet, thermocouple, and an overhead stirrer. The flask was charged with 2.20 Kg of 1-methyl-4-diethylsulfonamide-5-nitronaphthalene, along with ethanol (20 L).

Pd/C 10 wt % (50 wt % water wet, 0.17 Kg) was charged as a slurry in water (800 ml) and rinsed down with water (80 ml) and ethanol (6 L). To the resultant slurry was added potassium formate (1.74 Kg) in one portion. The slurry was warmed to 60° C. for 1 h then to reflux for 1 h.

The reaction was considered complete when <0.2% SM remained relative to the starting material as determined by HPLC.

On complete reaction the mixture was cooled to 20° C. and concentrated hydrochloric acid (2.73 L) added over about 20 min.

The resultant slurry was filtered through a pad of solka-floc™ and the cake washed with 10% hydrochloric acid in ethanol (total of 13 L). The combined filtrates were recharged to the cleaned 72 L flask and heated to reflux (81° C.) for 3–4 h to achieve complete cyclization.

The solution was cooled to 40° C. and concentrated to a slurry. The slurry was cooled to 20° C. and water (7.5 L) added over 30 min. The slurry was cooled to 5° C. and aged for 15 min.

The slurry was filtered and washed with water (5 L). The crystalline solid was dried under a stream of nitrogen overnight.

EXAMPLE 5

DILITHIATION-CARBOXYLATION

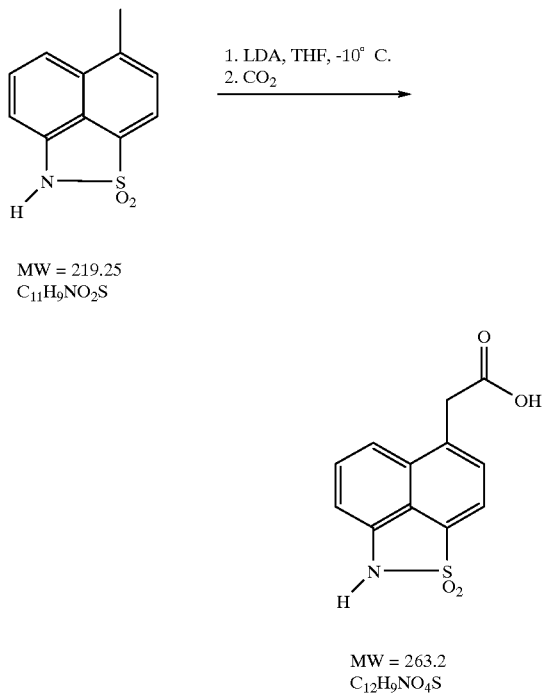

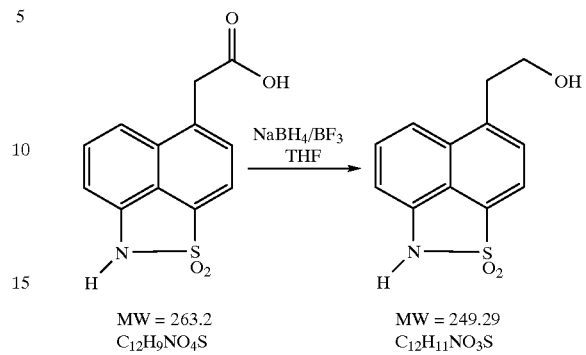

A 20 L flask equipped with nitrogen inlet, stirrer, temperature probe and addition funnel was charged with THF (5 L). Diisopropylamine(1.34 L) was added. The solution was cooled to −15° C. and n-butyllithium (6.0 L) added dropwise maintaining the reaction temperature between −15° C. and 0° C. to produce lithium diisopropylamide (LDA).

A separate 50 L flask equipped with stirrer and nitrogen inlet was charged with THF (10 L) and 1-Me NH naphthosultam (1.0 Kg). The solution was degassed by vacuum/purging with nitrogen and cooled to −15° C. and the LDA solution added dropwise keeping the solution temperature between −15° C. and −5° C. to produce the dianion solution.

The dianion solution was aged for 30 min at −15° C.

A separate 100 L flask equipped with stirrer, nitrogen inlet and temperature probe was charged with THF (10 L) and degassed with a vacuum/nitrogen purge. The solution was cooled to −20° C. and bone-dry grade $CO_2$ bubbled into the THF until saturation was reached. The dianion solution was then slowly added to this carbonated solution while ensuring efficient mixing of the resulting slurry. After warming to 10° C., 10 L of 2N HCl was added the solution and was aged for 30 min.

The solution was concentrated atmospherically to about 10 L to remove THF and initiate crystallization. The resultant slurry was aged at 15° C. for 30 min, filtered and the cake washed with water(10 L) and dried in a nitrogen stream.

EXAMPLE 6

BORANE REDUCTION

A 50 L round bottom flask was set up and equipped with a $N_2$ inlet, thermocouple, addition funnel and an overhead stirrer. The flask was charged with dried NH-sultam carboxylic acid (1.14 Kg) and THF (18 L). The slurry was cooled to 15° C. To this slurry was added $NaBH_4$ (327 g), followed by the slow addition of $BF_3$ etherate (1.42 L).

The slurry was aged at 15–20° C. and the reaction progress monitored by HPLC.

The slurry was cooled to 10° C. and methanol (1.2 L) slowly added to quench excess borane. 2N HCl (11 L) was added slowly and aged for 30 min. The quenched reaction mixture was distilled at atmospheric pressure to remove volatiles. The resultant solution was cooled to 55° C., seeded to initiate crystallization and cooled to 15° C. over 1 h. After aging for 30 min, the slurry was filtered, washed with 10 L water and dried under a stream of nitrogen.

EXAMPLE 7

DILITHIATION-HYDROXYMETHYLATION

A 10 mL flask equipped with nitrogen inlet, stirrer, and temperature probe was charged with THF (2 mL).

Diisopropylamine(0.14 mL) was added. The solution was cooled to −15° C. and n-butyllithium (0.66 mL) added dropwise maintaining the reaction temperature between −15° C. and 0° C. to produce lithium diisopropylamide (LDA).

A separate 20 mL flask equipped with stirrer and nitrogen inlet was charged with THF (2 mL) and 1-Me NH naphthosultam (0.07 gm). The solution was degassed by vacuum/purging with nitrogen and cooled to −15° C. and the LDA solution added dropwise keeping the solution temperature between −15° C. and −5° C. to produce the dianion solution.

The dianion solution was aged for 30 min at −15° C.

A separate 20 mL flask equipped with stirrer, nitrogen inlet and temperature probe was charged with THF (2 mL) and para formaldehyde (0.12 gm) and degassed with a vacuum/nitrogen purge. The solution was cooled to −20° C. The dianion solution was then slowly added to this parafomaldehyde solution while ensuring efficient mixing. After warming to 10° C., 10 mL of 2N HCl was added the solution and was aged for 30 min.

The solution was concentrated atmospherically to about 10 mL to remove THF and initiate crystallization. The resultant slurry was aged at 15° C. for 30 min, filtered and the cake washed with water(10 mL) and dried in a nitrogen stream.

What is claimed is:

1. A process for synthesizing a compound of formula I:

[Structure I: naphthalene with R at position 4, and a fused ring containing N-H and SO₂]

wherein R represents halo or $C_{1-6}$ alkyl, unsubstituted or substituted with OP, wherein P represents a protecting group, comprising:

(a) reacting a compound of the formula II:

[Structure II: naphthalene with R substituent]

wherein R is as previously defined, with chlorosulfonic acid to produce a compound of formula III:

[Structure III: naphthalene with R and SO₂Cl substituents]

(b) reacting compound III with $NHR^aR^b$, wherein $R^a$ and $R^b$ represent H or $C_{1-6}$ alkyl, to produce a compound of formula IV;

[Structure IV: naphthalene with R and $SO_2NR^aR^b$ substituents]

(c) reacting compound IV with $HNO_3$ to produce a compound of formula V:

[Structure V: naphthalene with R, $NO_2$, and $SO_2NR^aR^b$ substituents]

(d) reacting compound V with a reducing agent to produce a compound of formula VI:

[Structure VI: naphthalene with R, $NH_2$, and $SO_2NR^aR^b$ substituents]

and (e) reacting compound VI with acid to produce a compound of formula I.

2. A process in accordance with claim 1 wherein R represents methyl.

3. A process in accordance with claim 1 wherein R represents halo.

4. A process in accordance with claim 1 wherein one of $R^a$ and $R^b$ represent H or $C_{1-6}$ alkyl, and the other is $C_{1-6}$ alkyl.

5. A process in accordance with claim 4 wherein $R^a$ and $R^b$ represent $C_{1-6}$ alkyl.

6. A process in accordance with claim 5 wherein $R^a$ and $R^b$ represent ethyl.

7. A process in accordance with claim 1 wherein step (a) is conducted in a solvent selected from the group consisting of: nitromethane, nitrobenzene, dichlorobenzene, dichloromethane, chloroform, carbon tetrachloride, dichloroethane and trifluoroacetic acid.

8. A process in accordance with claim 7 wherein the solvent is trifluoroacetic acid.

9. A process in accordance with claim 7 wherein step (a) is conducted at a temperature of from about −40° C. to about 100° C.

10. A process in accordance with claim 1 wherein step (b) is conducted in a substantially non-reactive organic solvent.

11. A process in accordance with claim 10 wherein the solvent is selected from isopropanol, tertiary butanol, toluene, xylene, hexanes, ethers, esters, tetrahydrofuran, and chlorinated solvents selected from the group consisting of dichlorobenzene, dichloromethane, chloroform, carbon tetrachloride and dichloroethane.

12. A process in accordance with claim 11 wherein the temperature of the reaction of step (b) is between about −50° C. and reflux temperature.

13. A process in accordance with claim 1 wherein step (c) is conducted in a solvent selected from trifluoroacetic acid, sulfuric acid, nitrobenzene and a chlorinated organic solvent.

14. A process in accordance with claim 13 wherein step (c) is conducted at a temperature in the range of about −30° C. to about 60° C.

15. A process in accordance with claim 14 wherein step (c) is conducted at a temperature in the range of about 0 to about 20° C.

16. A process in accordance with claim 1 wherein step (d) is conducted at a temperature ranging from about −40° C. to reflux temperature.

17. A process in accordance with claim 16 wherein step (d) is conducted with a reducing agent which is selected from the group consisting of: hydrogen gas, formic acid or a derivative thereof selected from ammonium formate, a metal formate selected from sodium, potassium, lithium and calcium, tri-$C_{1-6}$ alkyl ammonium formate, sodium borohydride, cyclohexene and tin chloride.

18. A process in accordance with claim 1 wherein step (e) is conducted with an acid that is selected from the group consisting of hydrochloric, sulfuric, trifluoroacetic and methanesulfonic.

19. A process in accordance with claim 18 wherein the acid is hydrochloric.

* * * * *